US006957587B2

(12) United States Patent
Bitto et al.

(10) Patent No.: US 6,957,587 B2
(45) Date of Patent: Oct. 25, 2005

(54) VIBRATORY TRANSDUCER

(75) Inventors: Ennio Bitto, Aesch (CH); Christian Schütze, Basel (CH); Omar Momente, Liestal (CH)

(73) Assignee: Endress + Hauser Flowtech, AG, Reinach (CH)

( * ) Notice: Subject to any disclaimer, the term of this patent is extended or adjusted under 35 U.S.C. 154(b) by 0 days.

(21) Appl. No.: 10/229,291

(22) Filed: Aug. 28, 2002

(65) Prior Publication Data

US 2005/0039547 A1 Feb. 24, 2005

Related U.S. Application Data

(60) Provisional application No. 60/315,370, filed on Aug. 29, 2001.

(30) Foreign Application Priority Data

Aug. 29, 2001 (EP) .................................. 01120561
Feb. 20, 2002 (EP) .................................. 02003821

(51) Int. Cl.[7] .............................................. G01F 1/84
(52) U.S. Cl. ............................................. 73/861.355
(58) Field of Search ..................... 73/861.355, 861, 73/861.351, 861.354

(56) References Cited

U.S. PATENT DOCUMENTS

| 4,876,898 A | 10/1989 | Cage et al |
| 5,301,557 A | 4/1994 | Cage et al |
| 5,996,225 A * | 12/1999 | Ollila et al. ............ 73/861.357 |
| 6,286,373 B1 * | 9/2001 | Lister et al. ............ 73/861.355 |
| 6,711,958 B2 * | 3/2004 | Bitto et al. ............ 73/861.355 |

FOREIGN PATENT DOCUMENTS

| EP | 1001254 A1 | 5/2000 |
| WO | WO 01/33174 A1 | 5/2001 |

OTHER PUBLICATIONS

US 6,044,715, 04/2000, Ollila et al (withdrawn)

* cited by examiner

*Primary Examiner*—Edward Lefkowitz
*Assistant Examiner*—Takisha Miller
(74) *Attorney, Agent, or Firm*—Bacon & Thomas

(57) ABSTRACT

The transducer has a case which is formed by a support frame for supporting a fluid-conducting flow tube and by a case cap for encasing at least one bent segment of the flow tube which vibrates during operation of the transducer. The case cap comprises a channel-shaped first cap segment with a circular-arc-shaped first segment edge of predeterminable radius R and with an essentially identically shaped second segment edge. The first cap segment has a circular-arc-shaped cross section with a radius r less than the radius R of the first segment edge. The case cap further comprises an essentially plane second cap segment, which is connected via a circular-arc-shaped first segment edge with the first segment edge of the first cap segment, and a third cap segment, which is essentially mirror-symmetric with respect to the second cap segment and which is connected via a circular-arc-shaped first segment edge with the second segment edge of the first cap segment. The second and third segments each have a substantially greater flexural rigidity than the first cap segment. The use of the case cap permits the case of the transducer to be made as pressure-resistant as possible at minimum cost.

7 Claims, 3 Drawing Sheets

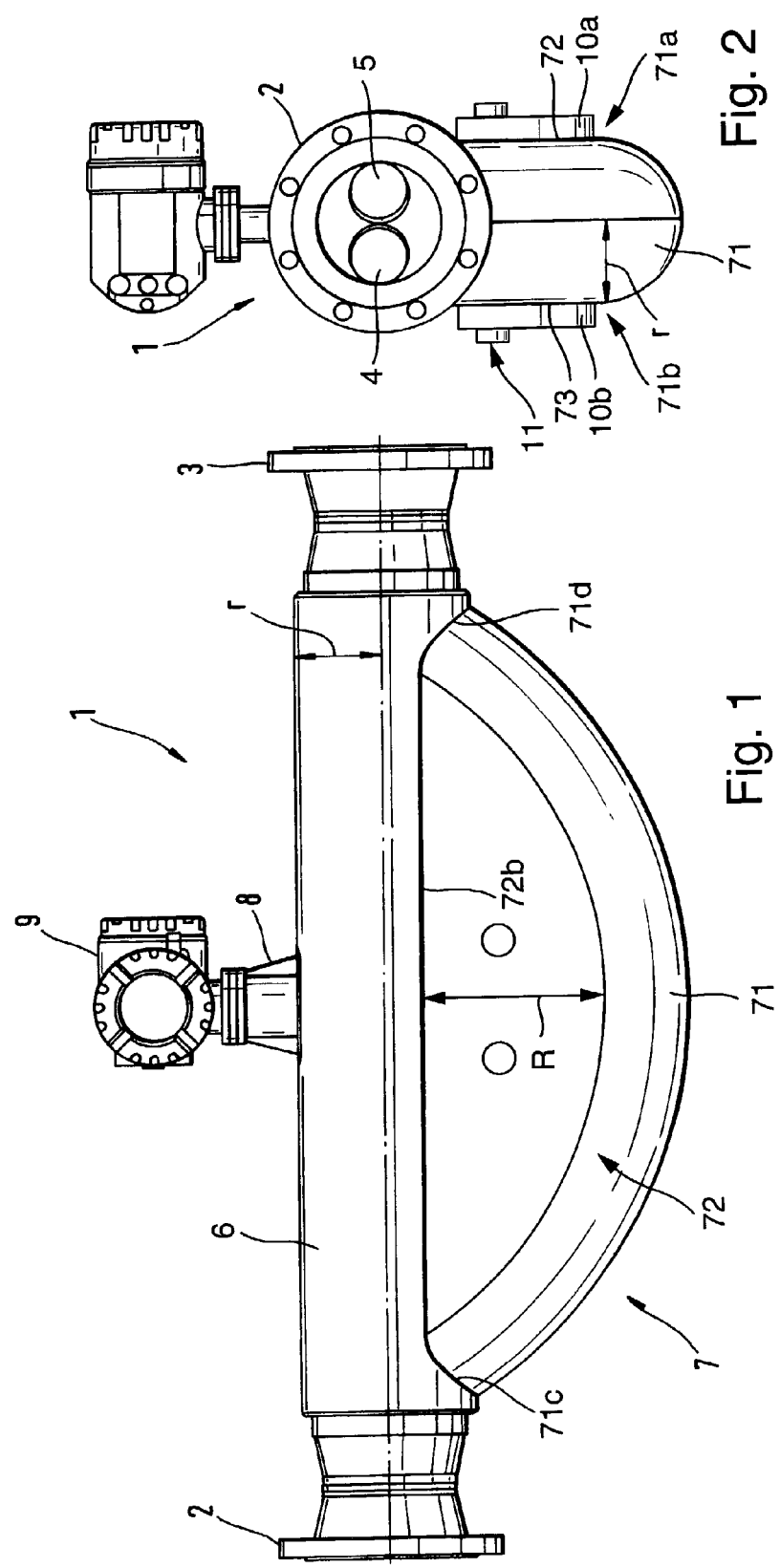

VIBRATORY TRANSDUCER

This application is based on Provisional Application No. 60/315,370, filed Aug. 29, 2001.

FIELD OF THE INVENTION

This invention relates to a case cap for a vibratory transducer and to a transducer using such a case cap.

BACKGROUND OF THE INVENTION

In process-measurement and automation technology, physical parameters of a fluid flowing in a pipe, such as mass flow rate, density, and/or viscosity, are frequently measured by means of meters which, using a vibratory transducer traversed by the fluid and a measuring and control circuit connected thereto, induce reaction forces in the fluid, such as Coriolis forces corresponding to the mass flow rate and inertial forces corresponding to the density, and derive therefrom a measurement signal representing the respective mass flow rate and/or density of the fluid.

Such mass flowmeters or Coriolis mass flowmeter-densiimeters are disclosed, for example, in WO-A 01/33174, WO-A 00/57141, WO-A 98/07009, U.S. Pat. No. 5,796,011, U.S. Pat. No. 5,301,557, U.S. Pat. No. 4,876,898, EP-A 553 939, EP-A 1 001 254, EP-A 553 939, EP-A 1 001 254, or European Patent Application EP 01 120 561.4, which was not published prior to the filing data of the present application. To conduct the fluid, each of the transducers comprises at least one flow tube held in a support frame and having a bent tube segment which in operation, driven by an electromechanical excitation assembly, is caused to vibrate in order to produce the above-mentioned reaction forces. To sense vibrations of the tube segment, particularly inlet-side and outlet-side vibrations, the transducers each comprise a sensor arrangement which responds to motions of the tube segment.

The flow tube as well as the excitation assembly and the sensor arrangement are enclosed by a case cap connected with, particularly welded to, the support frame. Besides supporting the at least one flow tube, the case, formed by the support frame and the case cap, serves in particular to protect the flow tube, the excitation assembly, and the sensor arrangement as well as other internal components from external environmental influences, such as dust or splashed water.

Such a case cap for a vibratory transducer for encasing at least one bent segment of a fluid-conducting flow tube, which segment vibrates during operation of the transducer, is disclosed, for example, in WO-A 00/57141, U.S. Pat. No. 5,301,557, EP-A 1 001 254, or European Patent Application EP 01 120 561.4. It comprises:
a channel-shaped first cap segment
  with a first segment edge and
  with a second segment edge essentially identical in shape to the first segment edge;
an essentially plane second cap segment
  which is connected via a first segment edge with the first segment edge of the first cap segment; and
a third cap segment, which is essentially mirror-symmetric with respect to the second cap segment and is connected via a first segment edge with the second segment edge of the first cap segment.

A requirement frequently placed by users on such transducer cases, particularly on the respective case caps, is that if the tube segment bursts, they can withstand the internal pressure, which is then generally well above the external pressure, without leaking for at least a predetermined time, see also WO-A 00/57141, U.S. Pat. No. 6,044,715, U.S. Pat. No. 5,301,557, or EP-A 1 001 254. At least for applications involving toxic or highly inflammable fluids, the case may also have to meet the requirements placed on a safety vessel.

While the required mechanical strength, particularly the required pressure resistance, can generally be readily provided by the support frame, particularly if the latter is in the form of a cylindrical tube, additional measures to increase the pressure resistance must be taken on the case caps because their three-dimensional shape is unfavorable for safety vessels.

The caps of such cases are generally integrally formed as deep-drawn semifinished products. They may also be composed of individual shell-shaped semifinished products which, as proposed in European Patent Application EP 01 120 561.4, for example, may be of small wall thickness, namely much less than 5 mm, or, as indicated in U.S. Pat. No. 6,044,715, for example, of greater wall thickness. While, as also stated in European Patent Application EP 01 120 561.4, case caps fabricated by deep drawing can be made economically only in large quantities because deep-drawing dies are very expensive, the composite case caps, which can be made at lower cost even in small numbers often do not have the required pressure resistances.

SUMMARY OF THE INVENTION

Starting from the above prior art, it is an object of the invention to provide a case suitable for a vibratory transducer which, on the one hand, can be manufactured at minimum cost and, on the other hand, is as pressure-resistant as possible.

To attain the object, the invention consists in a case cap for a vibratory transducer for encasing at least one bent tube segment of a fluid-conducting flow tube, which tube segment vibrates during operation of the transducer, said case cap comprising:
a channel-shaped first cap segment
  with a circular-arc-shaped first segment edge of predeterminable radius and
  with a second segment edge essentially identical in shape to the first segment edge,
  the first cap segment having a circular-arc-shaped cross section with a radius less than the radius of the first segment edge;
an essentially plane second cap segment,
  which is connected via a circular-arc-shaped first segment edge with the first segment edge of the first cap segment; and
a third cap segment, which is essentially mirror-symmetric with respect to the second cap segment and is connected via a circular-arc-shaped first segment edge with the second segment edge of the first cap segment,
  the second and third cap segments each having a substantially higher flexural rigidity than the first cap segment.

Furthermore, the invention consists in a transducer with said case cap wherein the latter is fixed via a third segment edge and a fourth segment edge of the first cap segment and via respective second segment edges of the second and third cap segments to a support frame for the flow tube in such a way that in operation, the cap segments remain spaced from the at least one vibrating tube segment.

In a first preferred embodiment of the case cap of the invention, the second and third cap segments each lie in one tangent plane of the first cap segment.

In a second preferred embodiment of the case cap of the invention, the second and third cap segments are provided with stiffening elements serving to set the necessary flexural rigidity.

In a third preferred embodiment of the invention, in order to increase the pressure resistance of the case cap, the latter comprises at least one clamping element which holds the second and third cap segments together tightly.

In a fourth preferred embodiment of the case cap of the invention, the clamping element is a tension bolt passing through the second and third cap segments.

In a fifth preferred embodiment of the case cap of the invention, the stiffening elements are stiffening plates of predeterminable thickness which are pressed against the cap segments by means of the tension bolt.

A fundamental idea of the invention is to design as large an area of the case cap as possible in such a way that an internal overpressure will produce essentially only tensile stresses in this selected area, so that the proportion of those areas in which bending stresses may occur is kept to a minimum. On the other hand, those particularly danger areas in which bending stresses may occur are designed so as to remain as dimensionally stable as possible even in the presence of an internal overpressure.

One advantage of the invention consists in the fact that because of the use of the channel-shaped and, hence, comparatively thin-walled cap segment and a rather slight mass increase as compared to, e.g., the case according to the above-mentioned European Patent Application EP 01 120 561.4, for instance through the use of additional stiffening and/or clamping elements in the areas of the two plane cap segments, a substantial increase in pressure resistance can be achieved. Investigations have shown that with a mass increase by about 20%, for instance through the use of side plates for the stiffening elements and of tension bolts for the clamping elements, and with virtually unchanged geometry, an increase in pressure resistance by more than 200% can be achieved.

BRIEF DESCRIPTION OF THE DRAWINGS

The invention will now be explained in more detail with reference to the accompanying drawings, which show a preferred embodiment of the invention. Throughout the various figures of the drawings, parts having similar functions are designated by the same reference characters, which, however, are repeated in subsequent figures only if this appears appropriate. In the drawings:

FIG. 1 is a side view of a transducer designed as a Coriolis-type flow/density/viscosity sensor;

FIG. 2 is a front view of the transducer of FIG. 1;

DETAILED DESCRIPTION OF EXEMPLARY EMBODIMENTS

Figure 3:
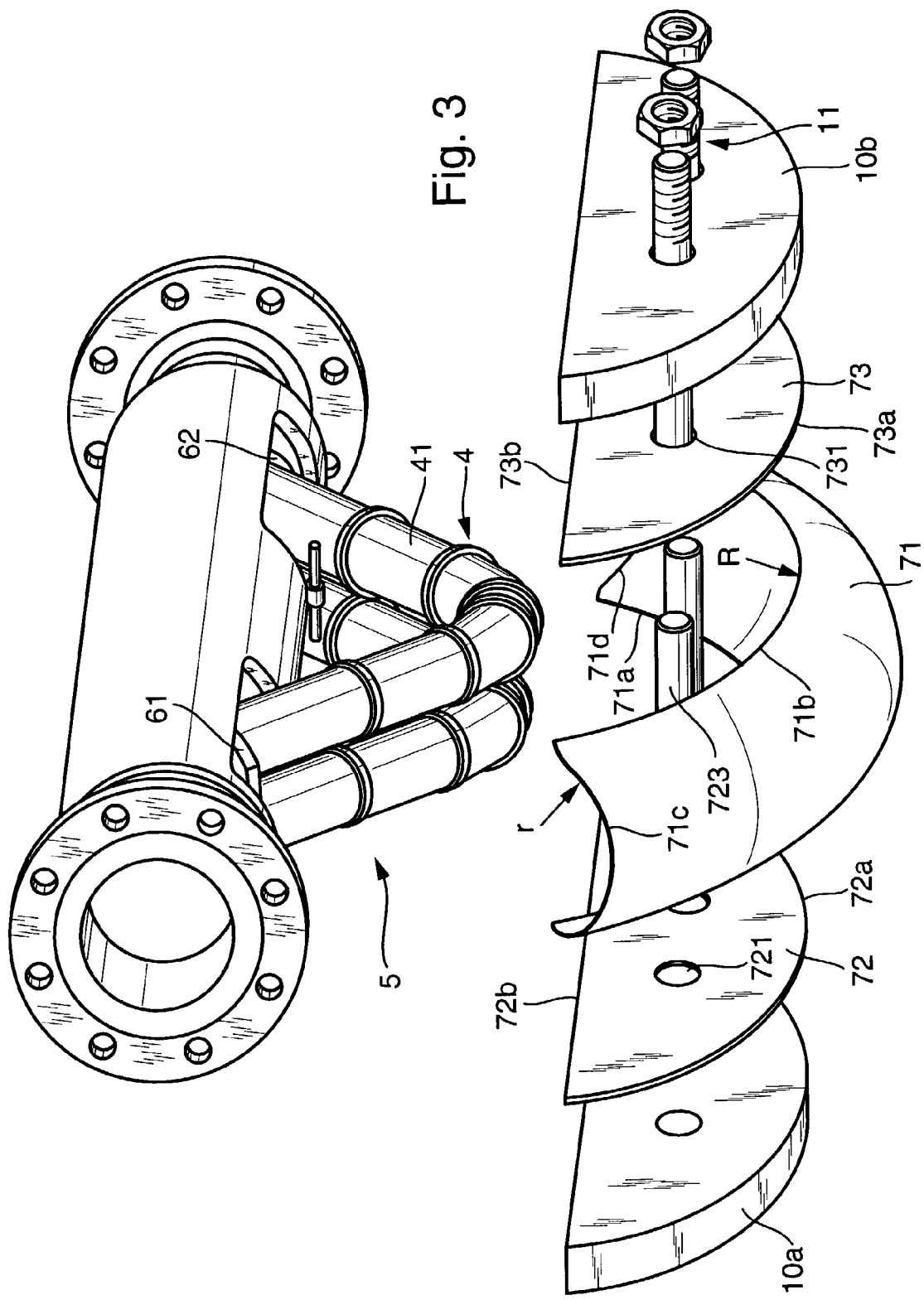
FIG. 3 is a partially exploded perspective view of the transducer of FIG. 1.

While the invention is susceptible to various modifications and alternative forms, exemplary embodiments thereof have been shown by way of example in the drawings and will herein be described in detail. It should be understood, however, that there is no intent to limit the invention to the particular forms diclosed, but on the contrary, the intention is to cover all modifications, equivalents, and alternatives falling within the spirit and scope of the invention as defined by the intended claims.

Figure 4:
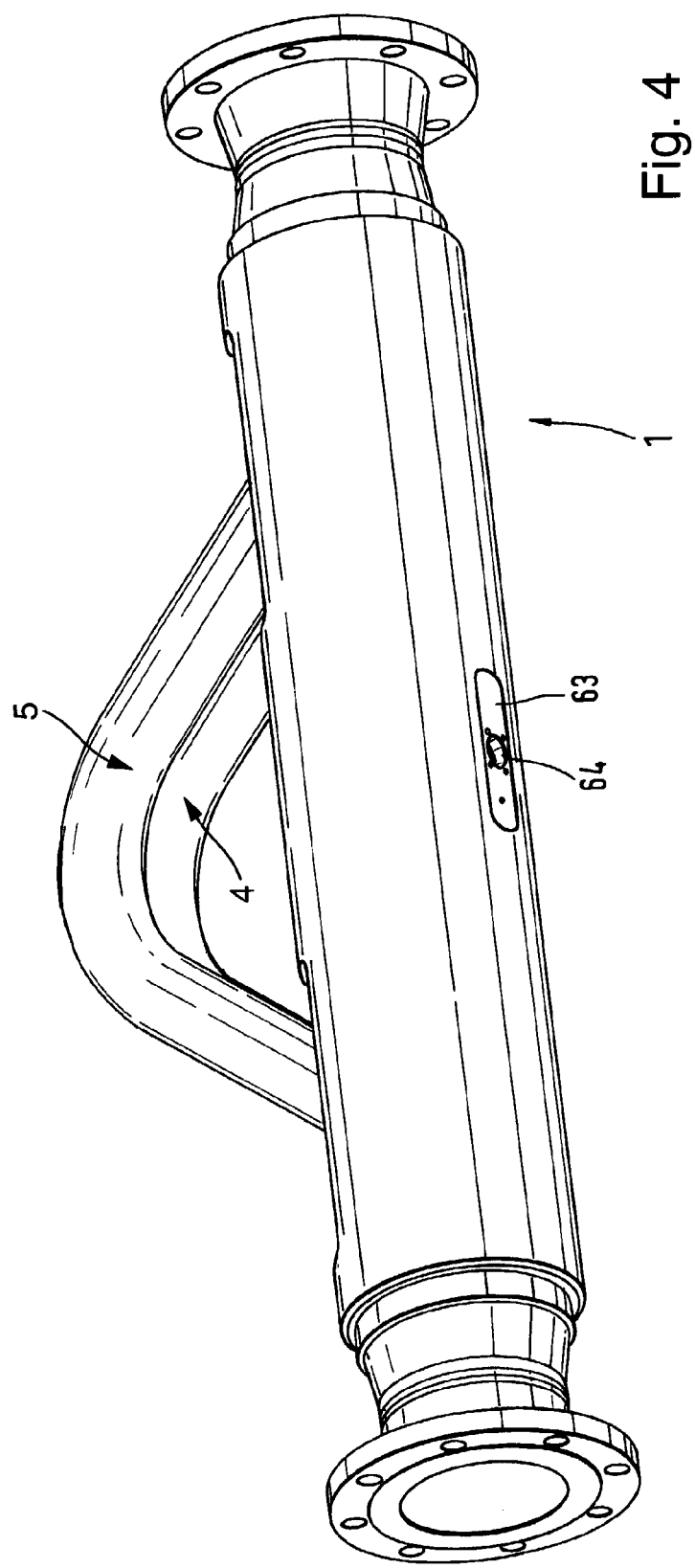
FIG. 4 is a partially broken perspective view of the transducer of FIG. 1.

FIGS. 1 to 4 show, in different representations, a vibratory transducer 1 serving in particular as a Coriolis mass flow, density, and/or viscosity sensor. FIG. 1 is a side view of transducer 1, FIG. 2 is a front view, and FIGS. 3 and 4 are perspective views of transducer 1 from two different angles. In the following, FIGS. 1 to 4 are explained together.

Transducer 1 is designed to be installed via flanges 2, 3 in a pipe (not shown for clarity) of a given diameter through which flows a liquid, gaseous, or vaporous fluid to be measured. Instead of flanges, other known means, such as Triclamp or threaded connections, may be used to connect transducer 1 to the pipe.

Transducer 1 has at least one flow tube 4 for conducting the fluid, with at least one tube segment 41 having at least one section bent in at least one plane; beside flow tube 4, an essentially identical, parallel second flow tube may be provided, as shown in FIGS. 3 and 4.

In operation, the segment 41 of flow tube 4 is excited by an excitation assembly (not shown), which is fixed, for instance at a vertex, into cantilever vibrations, preferably at an instantaneous mechanical resonance frequency, at which it is laterally deflected from the above-mentioned plane. In other words, tube segment 41 can be caused to vibrate in a flexural mode in the manner of a cantilever.

To sense vibrations of tube segment 41, a sensor arrangement (not shown) must be provided, by means of which vibrations of tube segment 41, particularly inlet-side and outlet-side vibrations, can be signaled to electronic processing circuitry in the usual manner.

Flow tube 4 is enclosed in a, preferably metallic, case consisting of a support frame 6 and a case cap 7. Materials suitable for the case, particularly for case cap 7, are structural steels or stainless steels, for example.

As shown in FIG. 3, flow tube 4 is held on the inlet and outlet sides in support frame 6, here a tubular frame, such that the oscillable tube 41, extending through two openings 61, 62 in support frame 6, projects laterally from the latter and thus into case cap 7, which is fixed to support frame 6.

The case serves, on the one hand, to protect the internal components of transducer 1, such as flow tube 4, the excitation assembly, and the sensor arrangement, from external environmental influences, such as dust or splashed water, and, on the other hand, in case of any damage to flow tube 4 or flow tube 5, for instance due to cracking or bursting, to keep as much leaking fluid as possible inside the case up to a required maximum overpressure.

FIG. 1 also shows an electronics case 9 which is fixed to support frame 6, here to the supporting tube, by means of a necklike transition piece 8 and which houses a measuring and control circuit of transducer 1; this circuit generates an excitation signal for the aforementioned excitation assembly, receives the signals from the aforementioned sensor arrangement, and derives therefrom the desired signals representing the mass flow rate, density, viscosity, or temperature of the flowing fluid. These signals can be further processed or indicated.

In FIGS. 3 and 4, transition piece 8 and electronics case 9 have been omitted; in FIG. 4, an attachment area 63 for transition piece 8 can be seen. Attachment area 63 contains a bushing 64 through which electric connections can be made to the above-mentioned excitation assembly and the above-mentioned sensor arrangement as well as to any further electric components that may be present, such as temperature sensors.

As shown schematically in FIG. 3, case cap 7, which serve to encase tube segment 41, comprises a channel-shaped first cap segment 71, an essentially plane second cap segment 72, and a third cap segment 73, which is essentially mirror-symmetric with respect to the second cap segment 72. The shape of cap segment 71 corresponds essentially to that of a toroidal shell, as is readily apparent from FIG. 3. Accordingly, cap segment 71 has an essentially circular-arc-shaped, preferably semicircular, cross section of predeterminable radius r and, at least virtually, an essentially circular-arc-shaped first segment edge 71a with a radius R substantially greater than radius r as well as an essentially identically shaped second segment edge 71b. If necessary, both the cross section and the segment edge may not be ideally circular, i.e., they may be slightly elliptic, at least to the extent that the elasticity and/or ductility of the material of case cap 7 are chosen so that case cap 7 responds to a rising internal pressure at most with an adaptation of the shape of cap segment 71 to that of an ideal toroidal shell.

According to the invention, therefore, the lateral cap segments 72, 73 each have a substantially higher flexural rigidity than the channel-shaped cap segment 71, whereby a high dimensional stability, particularly at a maximum permissible internal overpressure, of cap segments 72, 73, which may be subjected to bending stress, and, thus, a substantial improvement in the pressure resistance of the entire case cap 7 are achieved.

As is readily apparent when FIGS. 1, 2, and 3 are viewed together, cap segments 72 and 73 are connected via circular-arc-shaped first segment edges 72a and 73a with the first segment edge 71a of cap segment 71 and the second segment edge 71b of cap segment 71, respectively, preferably such that cap segments 72, 73 each lie in one tangent plane of cap segment 71 and are thus aligned with tangents to the associated segment edges 71a and 71b, respectively. In other words, between the two cap segments 71, 72 and the two cap segments 71, 73, as smooth a transition as possible is to be provided in which no or very small bending stresses are produced at a permissible internal overpressure. In addition, case cap 7 is fixed via a third segment edge 71c and a fourth segment edge 71d of cap segment 71 and via respective second and third segment edges 72b, 73b of the second and third cap segments 72, 73 to support frame 6 in such a way that in operation, cap segments 71, 72, 73 remain spaced from the at least one vibrating tube segment 41.

The use of cap segments 71, 72, 73 shaped as described above is based in particular on recognition that, on the one hand, pressure vessels with walls subjected exclusively to tensile stress can have a far higher pressure resistance than those with walls of comparable thickness which are subjected to bending stress, while on the other hand, an ideal pressure vessel, namely a vessel in the form of a hollow sphere, is not realizable for transducers of the kind described.

Since one area of the case cap, namely the cap segment 71, is subjected only to tensile stress, a high pressure resistance can be achieved for the case cap 7 despite a comparatively small wall thickness in this area of just a few millimeters, particularly less than 5 mm. Consequently, measures designed to increase the flexural rigidity of case cap 7 for the purpose of increasing the pressure resistance of the case can advantageously remain confined to cap segments 72, 73, whose share of the total surface of case cap 7 can, in turn, be readily kept to a minimum within the scope of the specified mounting dimensions.

In other words, the size of cap segment 71, which is subjected essentially only to tensile stress, can be so optimized that the transducer using the case cap 7 according to the invention remains as compact as possible but in any case can have mounting dimensions in the range of those of comparable conventional vibratory transducers. Furthermore, the mass increase associated with the provision of stiffening elements 10a, 10b (see below) can be kept small in comparison with conventional case caps of comparable pressure resistance.

To form case cap 7, the cap segments 71, 72, 73 may, for instance, be prefabricated separately and then be joined together, particularly welded together. Advantageously, use can be made of the method described in the above-mentioned European Patent Application EP 01 120 561.4 for producing a metal cap usable as case cap 7, in which the latter is formed by welding together two essentially identically shaped cap halves with a, particularly quarter-torus-shaped, beaded edge, the cap halves being preferably cut out of a plate-shaped semifinished product. Case cap 7 may also be a deep-drawn sheet metal part of suitable thickness, for example.

In a further preferred embodiment of the invention, the increased flexural rigidity, and hence the high dimensional stability, of cap segments 72, 73 is achieved by providing them with stiffening elements 10a, 10b. Stiffening elements 10a, 10b may be, for instance, plates or strips fixed to cap segments 72, 73 or crimps formed on cap segments 72, 73.

In yet another preferred embodiment of the invention, the high flexural rigidity of cap segments 72, 73 is achieved by providing the case 7 with at least one clamping element 11 which holds the two cap segments 72, 73 together tightly.

In still another preferred embodiment of the invention, clamping element 11 is a tension bolt which, as can be seen in FIGS. 2 and 3, is passed through opposite holes 721, 731 in cap segments 72, 73 and through corresponding holes in the plates serving as stiffening elements 10a, 10b, and which, fastened by means of clamp nuts, holds the two cap segments 72, 73 together tightly.

As shown in FIG. 3, case cap 7 is held in the area of holes 721, 731 in a fluid-tight manner by means of a connecting tube 723 communicating with holes 721, 731 and joined, e.g., welded, to the edges of these holes.

One of the advantages of this embodiment of the invention is that, compared with conventional cases, a fluid-tight, but not necessarily heavily loadable portion of case cap 7 is first formed at no significant additional production cost, which can be made pressure-resistant up to a predeterminable overpressure, particularly an overpressure predeterminable in steps, by subsequently, particularly detachably, fixing heavily loadable attachments. This embodiment of the invention can also be used to advantage with existing case concepts, so that the pressure resistance of conventional cases can also be substantially improved at little additional production and assembly cost.

While the invention has been illustrated and described in detail in the drawings and forgoing description, such illustration and description is to be considered as exemplary not restrictive in character, it being understood that only exemplary embodiments have been shown and described and that all changes and modifications that come within the spirit and scope of the invention as described herein are desired to protected.

What is claimed is:

1. A case cap for a vibratory transducer for encasing at least one bent tube segment of a fluid-conducting flow tube, which tube segment vibrates during operation of the transducer, said case cap comprising:

a channel-shaped first cap segment, with a circular-arc-shaped first segment edge of predeterminable radius and a second segment edge essentially identical in shape to said first segment edge, said first cap segment having a circular-arc-shaped cross section with a radius less than the radius of said first segment edge;

an essentially plane second cap segment, which is connected via a circular-arc-shaped first segment edge with said first segment edge of said first cap segment; and a third cap segment, which is essentially mirror-symmetric with respect to said second cap segment and is connected via a circular-arc-shaped first segment edge with said second segment edge of said first cap, wherein:

said second and third cap segments each having a substantially higher flexural rigidity than said first cap segment.

2. The case cap as set forth in claim 1, wherein:

said second and third cap segments each lie in one tangent plane of the first cap segment.

3. The case cap as set forth in claim 1, wherein:

said second and third cap segments are provided with stiffening elements serving to set the necessary flexural rigidity.

4. The case cap as set forth in claim 1, further comprises:

at least one clamping element which holds said second and third cap segments together tightly in order to increase its pressure resistance.

5. The case cap as set forth in claim 4, wherein:

said clamping element is a tension bolt passing through said second and third cap segments.

6. The case cap as set forth in claim 5, wherein:

said stiffening elements are stiffening plates which are pressed against said second and third cap segments, respectively, by means of said tension bolt.

7. The transducer comprising a case cap as set forth in claim 1, wherein:

the case cap is fixed via a third segment edge and a fourth segment edge of said first cap segment and via respective second segment edges of said second and third cap segments to a support frame for the flow tube in such a way that in operation, said first, second, and third cap segments remain spaced from the at least one vibrating tube segment.

* * * * *